United States Patent
Bonrath et al.

(10) Patent No.: US 6,482,961 B2
(45) Date of Patent: Nov. 19, 2002

(54) METHOD OF MAKING (ALL-RAC)-α-TOCOPHEROL

(75) Inventors: Werner Bonrath, Freiburg (DE); Alois Haas, Bochum (DE); Eike Hoppmann, Leipzig (DE); Horst Pauling, Aesch (CH)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/931,663

(22) Filed: Aug. 16, 2001

(65) Prior Publication Data

US 2002/0072619 A1 Jun. 13, 2002

(30) Foreign Application Priority Data

Aug. 18, 2000 (EP) .............................. 00117761

(51) Int. Cl.$^7$ ............................. C07D 311/04
(52) U.S. Cl. .................................... 549/408
(58) Field of Search .................. 549/408, 407

(56) References Cited

U.S. PATENT DOCUMENTS

| 5,273,840 A | 12/1993 | Dominey ................ 429/192 |
| 5,554,664 A | 9/1996 | Lamanna et al. ............ 522/25 |

FOREIGN PATENT DOCUMENTS

| EP | 0 658 552 A1 | 6/1995 |
| EP | 0 949 255 A1 | 10/1999 |
| EP | 1 000 940 A1 | 5/2000 |
| WO | WO 98/21197 | 5/1998 |

OTHER PUBLICATIONS

Ishihara, et al., "Practical Synthesis of (±)-α-Tocopherol. Trifluoromethanesulfonimide as an Extremely Active Brønsted Acid Catalyst for the Condensation of Trimethylhydroquinone with Isophytol," Synlett, pp. 1045–1046 (Nov. 1996).

Nishikido, et al., "Scandium and Ytterbium Tris(perfluorobutanesulfonyl)methide Complexes: Extremely Efficient Lewis Acid Catalysts," Synlett, No. 12, pp. 1990–1992 (1999).

Waller, et al., "Tris(trifluoromethanesulfonyl)methide ("Triflide") Anion: Convenient Preparation, X–ray Crystal Structures, and Exceptional Catalytic Activity as a Counterion with Ytterbium(III) and Scandium(III)," J. Org. Chem., vol. 64, pp. 2910–2913 (1999).

*Primary Examiner*—Amelia Owens
(74) *Attorney, Agent, or Firm*—Bryan Cave LLP

(57) ABSTRACT

The present invention is a method of making (all-rac)-α-tocopherol in a reaction having the following steps:

a) reacting trimethylhydroquinone and a phytol selected from the group consisting of isophytol and phytol in the presence of a bis(perfluorinated hydrocarbyl sulphonyl) imide catalyst or a metal salt thereof of formula I:

$$[(R^1SO_2)_2N]_xR^2 \qquad (I)$$

wherein
each $R^1$, independently, signifies a perfluoroalkyl group $C_nF_{2n+1}$ or a pentafluorophenyl, or both symbols $R^1$ together signify a poly-difluoromethylene group—$(CF_2)_m$—, with the proviso that both symbols $R^1$ cannot simultaneously signify trifluoromethyl, $R^2$ signifies a proton or a cationic form of a metal selected from the group consisting of boron, magnesium, aluminum, silicon, scandium, titanium, vanadium, manganese, iron, cobalt, nickel, copper, zinc, yttrium, zirconium, rhodium, palladium, silver, tin, lanthanum, cerium, praseodymium, neodymium, europium, dysprosium, thulium, ytterbium, hafnium, platinum, and gold, m is an integer from 2 to 4, n is an integer from 1 to 10, and x is the corresponding valency of the proton (1) or the metal cation (1, 2, 3, or 4), in organic solvent; and b) recovering (all-rac)-α-tocopherol from the reaction mixture.

20 Claims, No Drawings

METHOD OF MAKING (ALL-RAC)-α-TOCOPHEROL

FIELD OF THE INVENTION

The present invention is a method of making (all-rac)-α-tocopherol by the acid-catalyzed reaction of trimethylhydroquinone (TMHQ) with isophytol (IP) or phytol (PH) in a solvent.

BACKGROUND OF THE INVENTION (All-rac)-α-tocopherol (or, as it is generally known, "d,1-α-tocopherol") is a diastereoisomeric mixture of 2,5,7,8-tetramethyl-2-(4',8',12'-trimethyl-tridecyl)-6-chromanol (α-tocopherol), which is the most active and most industrially important member of the vitamin E group.

Many processes for the manufacture of "d,1-α-tocopherol by the reaction of TMHQ with IP or PH in the presence of a catalyst or catalyst system and in a solvent or solvent system are described in the literature. These processes go back to the work of Karrer et al., Bergel et al., as well as Smith et al. (see Helv. Chim. Acta 21, 520 et seq. (1938), Nature 142, 36 et seq. (1938) and, respectively, Science 88, 37 etseq. (1938) and J. Am. Chem. Soc. 61, 2615 et seq. (1939)). While Karrer et al. carried out the synthesis of d,1-α-tocopherol from TMHQ and phytyl bromide in the presence of anhydrous zinc chloride ($ZnCl_2$; a Lewis acid), not only Bergel et al. but also Smith et al. used TMHQ and PH as starting materials. In the following years mainly modifications, e.g. alternative solvents and Lewis acids, were developed. In 1941, a process for the manufacture of d,1-α-tocopherol which was based on the reaction of TMHQ with IP in the presence of the catalyst system $ZnCl_2$/hydrochloric acid (HCl) was developed from the work of Karrer et al. (U.S. Pat. No. 2,411,969). Later publications, e.g. Japanese Patent Publications (Kokai) 54380/1985, 64977/1985, and 226979/1987 (Chemical Abstracts (C.A.) 103, 123731s (1985), C.A. 103, 104799d (1985) and, respectively, C.A. 110, 39217r (1989)), describe this reaction in the presence of zinc and/or $ZnCl_2$ and a Bronsted (protonic) acid, such as a hydrohalic acid, e.g., HCl, trichloroacetic acid, acetic acid, and the like, especially $ZnCl_2$/HCl, as the catalyst system. The disadvantages of these and further published processes featuring $ZnCl_2$ in combination with a Bronsted acid are the corrosive properties of the acid and the contamination of the waste water with zinc ions as a result of the large amount of $ZnCl_2$ required for the catalysis.

The manufacture of d,1-α-tocopherol by the reaction of TMHQ with phytyl chloride, PH, or IP in the presence of boron trifluoride ($BF_3$) or its etherate ($BF_3.Et_2O$) is described in German Patents 960720 and 1015446 as well as in Nelan, U.S. Pat. No. 3,444,213. However, $BF_3$ also has corrosive properties.

Also, the reaction of TMHQ with IP or PH in the presence of a Lewis acid, e.g., $ZnCl_2$, $BF_3$, or aluminum trichloride ($AlCl_3$), a strong acid, e.g. , HCl, and an amine salt as the catalyst system is described in European Patent Publication (EP) 100471. In an earlier patent publication, DOS 2606830, the IP or PH is pretreated with ammonia or an amine before the reaction with TMHQ in the presence of $ZnCl_2$ and an acid is carried out. In both cases corrosion problems persist.

A further interesting method for the manufacture of d,1-α-tocopherol from TMHQ and IP uses an isolated TMHQ—$BF_3$ or —$AlCl_3$ complex and a solvent mixture featuring a nitro compound (DOS 1909164). This process avoids, to a large extent, the formation of undesired by-products because it involves mild reaction conditions. The yield of d,1-α-tocopherol, based on IP and the use of the solvent mixture methylene chloride/nitro-methane, is given as 77%. Accordingly, the use of such a solvent mixture is disadvantageous.

The manufacture of d,1-α-tocopherol by the reaction of TMHQ with IP using cation exchange resin complexes of metal ions ($Zn^{2+}$, $Sn^{2-}$, and $Sn^{4+}$) is disclosed in Bull. Chem. Soc. Japan 50, 2477–2478 (1977), among other disadvantages, it produces the product in unsatisfactory yields.

The use of macroreticular ion exchangers, e.g., AMBERLYST® 15, as the catalyst for the reaction of TMHQ with IP is described in Moroe et al., U.S. Pat. No. 3,459,773. However, the d,1-α-tocopherol could not be obtained in the requisite purity.

EP 603695 describes the manufacture of d,1-α-tocopherol in liquid or supercritical carbon dioxide by the reaction of TMHQ with IP or PH in the presence of acidic catalysts, such as $ZnCl_2$/HCl and ion exchangers. However, the reported yields are unsatisfactory.

The reaction in the presence of a catalyst system which consists of iron(II) chloride, metallic iron, and HCl gas or aqueous solution is described in DOS 2160103 and Heinrich et al., U.S. Pat. No. 3,789,086. Although this method forms less by-products, corrosion problems and chloride contamination remain as disadvantages.

An interesting alternative for the reaction of TMHQ with IP to d,1-α-tocopherol uses trifluoroacetic acid or its anhydride as the catalyst (EP 12824). Although no HCL is used in this process, the catalyst is expensive.

The use of the heteropoly acid 12-tungstophosphoric or 12-tungstosilicic acid as the catalyst for the reaction of TMHQ with IP was described for the first time in React. Kinet. Catal. Lett. 47(1), 59-64 (1992). d,1-α-Tocopherol was obtained, using various solvents, in about 90% yield.

A further process described in the literature (EP 658552; Bull. Chem. Soc. Japan 68, 3569–3571 (1995)) for the synthesis of d,1-α-tocopherol is based on the use of various lanthanide trifluoromethanesulphonates (triflates), e.g., scandium trifluoromethanesulphonate, as the catalyst for the reaction. With up to about 10% excess of IP this process produces yields of up to 98%.

The use of ion-exchanged bentonite, montmorillonite, or saponite through treatment with, e.g., scandium chloride and other metal salts (yttrium, lanthanum, etc.) as the catalyst for the reaction of TMHQ with IP or PH, has the disadvantage of requiring a large amount of catalyst (EP 677520; Bull. Chem. Soc. Japan 69, 137–139 (1996)).

According to the Examples of EP 694541 the reaction of TMHQ with IP to α-tocopherol can be achieved in high yields and with a high product purity when such solvents as carbonate esters, fatty acid esters, and certain mixed solvent systems are employed, the exemplified catalysis being effected by $ZnCl_2$/HCl. The disadvantage in this process, in addition to the contamination of the waste water by zinc ions, is the usual large "catalyst amount" of $ZnCl_2$ required.

According to WO 97/28151 the acid-catalyzed reaction of TMHQ with IP can be performed in a cyclic carbonate or α-lactone as the solvent. The preferred catalyst is a mixture of orthoboric acid and oxalic, tartaric, or citric acid, or boron trifluoride etherate.

WO 98/21197 describes the manufacture of d,1-α-tocopherol from TMHQ and IP using bis (trifluoromethylsulphonyl)imide or a metal salt thereof optionally together with a strong Bronsted acid, as catalyst in such types of aprotic solvents as aliphatic and cyclic ketones or esters, and aromatic hydrocarbons.

Using the same kind of bis(trifluoromethylsulphonyl) imide catalyst it has been shown (EP 1000940) that the d,1-β-tocopherol manufacturing process can also be realized when supercritical carbon dioxide or nitrous oxide is used as the solvent.

From the forgoing review it is evident that most of the previously known processes have considerable disadvantages. Corrosion problems occur in all processes in which acid catalysts such as boron trifluoride are used. Toxicity problems with the boron trifluoride adducts also occur, and when iron or zinc is used there is a contamination of the waste water with the metal ions which is today no longer acceptable. In some processes the formation of undesired by-products, e.g., phytyltoluene and chlorophytols, is an especially serious problem. Finally, in most cases the product yields are unsatisfactory.

SUMMARY OF THE INVENTION

An object of the present invention is to provide a process for the manufacture of (all-rac)-α-tocopherol by the reaction of trimethylhydroquinone with isophytol or phytol in the presence of a catalyst and in a solvent which does not have the disadvantages of previously known procedures. In this respect, it is necessary that the catalyst used has no, or at least a much reduced, corrosive action, is non-toxic, does not contaminate the environment, e.g., with chlorinated by-products or heavy metal ions, and catalyzes the desired reaction as selectively as possible and in high yields. Furthermore, the catalyst should display its activity in small, truly catalytic, amounts and should be readily separable and re-usable several times.

One embodiment of the present invention is a method of making (all-rac)-α-tocopherol in a reaction mixture having the following steps:

a) reacting trimethylhydroquinone and a phytol selected from the group consisting of isophytol and phytol in the presence of a bis(perfluorinated hydrocarbyl sulphonyl) imide catalyst or a metal salt thereof of formula I:

$$[(R^1SO_2)_2N]_xR^2 \qquad (I)$$

wherein each $R^1$, independently, signifies a perfluoroalkyl group $C_nF_{2n+1}$ or a pentafluorophenyl, or both symbols $R^1$ together signify a poly-difluoromethylene group —$(CF_2)_m$—, with the proviso that both symbols $R^1$ cannot simultaneously signify trifluoromethyl, $R^2$ signifies a proton or a cationic form of a metal selected from the group consisting of boron, magnesium, aluminium, silicon, scandium, titanium, vanadium, manganese, iron, cobalt, nickel, copper, zinc, yttrium, zirconium, rhodium, palladium, silver, tin, lanthanum, cerium, praseodymium, neodymium, europium, dysprosium, thulium, ytterbium, hafnium, platinum, and gold, m is an integer from 2 to 4, n is an integer from 1 to 10, and x is the corresponding valency of the proton (1) or the metal cation (1, 2, 3, or 4), in organic solvent; and b) recovering (all-rac)-α-tocopherol from the reaction mixture.

DETAILED DESCRIPTION OF THE INVENTION

The reaction itself is represented in the following Reaction Scheme, showing the reaction with IP only.

Reaction Scheme

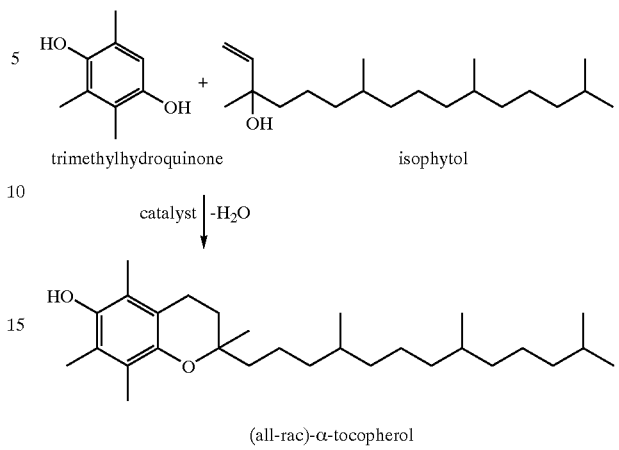

trimethylhydroquinone        isophytol

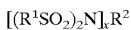
(all-rac)-α-tocopherol

Accordingly, the process in accordance with the present invention for the manufacture of (all-rac)-α-tocopherol by the catalyzed reaction of trimethyhydroquinone with isophytol or phytol is characterized by carrying out the reaction in the presence of a bis(perfluorinated hydrocarbyl sulphonyl)imide or a metal salt thereof of the general formula $$[(R^1SO_2)_2N]_xR^2 \qquad I$$

wherein each $R^1$, independently, signifies a perfluoroalkyl group $C_nF_{2n+1}$ or pentafluorophenyl, or both symbols $R^1$ together signify a poly-difluoromethylene group —$(CF_2)_m$—, with the proviso that both symbols $R^1$ cannot simultaneously signify trifluoromethyl, $R^2$ signifies a proton or a metal cation selected from the group consisting of boron, magnesium, aluminium, silicon, scandium, titanium, vanadium, manganese, iron, cobalt, nickel, copper, zinc, yttrium, zirconium, rhodium, palladium, silver, tin, lanthanum, cerium, praseodymium, neodymium, europium, dysprosium, thulium, ytterbium, hafnium, platinum and gold, each in the cationic form, m signifies an integer from 2 to 4, n signifies an integer from 1 to 10, and x signifies the corresponding valency of the proton (1) or metal cation (1, 2, 3 or 4), as the catalyst in an organic solvent.

Not only some of the above-defined bis(perfluorinated hydrocarbyl sulphonyl)imides, but also some of their metal salts amongst the catalysts of formula I are known compounds. Those catalysts of formula I which may still not be known can be produced by methods analogous to the published methods for producing bis (trifluoromethylsulphonyl)imide and its metal salts (excluded from the scope of the catalysts of formula I by the proviso) and the higher members of these sulphonimides and their metal salts: see e.g., EP 364340/Armand, U.S. Pat. No. 5,256,821, Japanese Patent Publications (Kokai) 246338/1995, 064238/1996 (with the US counterpart Yoshihiro et al., U.S. Pat. No. 5,650,244), 057110/1997, 169690/1997, 176063/1997, 176171/1997, 241184/1997, 230166/1998, 330314/1998, and 209338/1999, DOS 4217366/Klaus et al., U.S. Pat. No. 5,502,251, DOS 19533711/Sakaguchi et al., U.S. Pat. No. 5,723,664, Chemiker Zeitung 96, 582–583

(1972), Chem. Lett. 1995, 307–308, Synlett 1996, 171–172, 265–266, and 839–841, Inorg. Chem. 35(7), 1918–1925 (1996), J. Power Sources 68, 307–310 (1997), and Cat. Today 36(81–84 (1997) as well as the further literature references summarized above. For example, many of the salts can be produced from the appropriate bis (perfluorinated hydrocarbyl sulphonyl)imide of formula I in which $R^2$ signifies a proton and the metal acetates, oxides, hydroxides, and alcoholates featuring the desired metal cation. In the case of the aluminium, zinc, and various other metal salts these can also be produced using the corresponding alkylmetal or dialkylmetal hydride, e.g., diethylzinc or triethylaluminium or, respectively, diisobutylaluminium hydride.

In some cases the metal salts can be present in monomeric or polymeric form and, accordingly, formula I is intended to embrace all such forms. Further, these catalysts can be used in isolated form or produced in situ.

Examples of a catalyst of formula I in which the symbols $R^1$ together signify a polydifluoromethylene group $-(CF_2)_m-$ are 4,4,5,5,6,6-hexafluoro-(1,3,2)dithiazinane-1,3-dioxide and its silver salt.

The metal salts of the above-defined catalysts of formula I can be used together with a strong Brønsted acid as a co-catalyst in the process of the present invention. The Brønsted acid present in such a catalyst system can be an inorganic or organic acid, examples of which are sulphuric acid, phosphoric acid, and p-toluenesulphonic acid.

Solvents which can be used in the scope of the present invention are polar or non-polar organic solvents. Suitable classes of polar solvents include aliphatic and cyclic ketones, e.g., diethyl ketone and isobutyl methyl ketone and, respectively, cyclopentanone and isophorone; and aliphatic and cyclic esters, e.g., ethyl acetate and isopropyl acetate, and, respectively, γ-butyrolactone, ethylene carbonate, and propylene carbonate. As suitable classes of non-polar solvents include aliphatic hydrocarbons, e.g., hexane, heptane and octane, and aromatic hydrocarbons, e.g., benzene, toluene and the xylenes. The reaction can be effected in a single solvent phase, e.g., in toluene alone as the solvent, or in a biphasic solvent system, e.g., in ethylene or propylene carbonate and heptane.

The method is conveniently effected (i.e., carried out) at temperatures from about 50° C. to about 150° C., preferably from about 90° C. to about 125° C., and more preferably from about 105° C. to about 120° C.

In the present invention, the term "phytol" means the presence of either isophytol or phytol in the reaction mixture.

Furthermore, the molar ratio of trimethylhydroquinone to the phytol present in the reaction mixture is from about 1.3:1 to about 2.5:1, preferably from about 1.5:1 to about 2.2:1, and is more preferably is about 2:1.

The amount of catalyst of formula I used is such that the molar ratio of catalyst to the educt (trimethylhydroquinone or the phytol) which is in the lesser molar amount (usually the phytol rather than the trimethylhydroquinone) is conveniently about 0.01:100 to about 4:100, i.e. the amount of catalyst is conveniently from about 0.01 mole % to about 4 mole % of the amount of educt in the lesser molar amount. Where a catalyst system (combination of a metal salt of formula I and a strong Brønsted acid) is used, the amount of metal salt is conveniently about 0.1 mole % to about 4 mole % and the amount of Brønsted acid is conveniently about 0.01 mole % to about 0.5 mole %, in each case based on the amount of educt in the lesser molar amount.

Conveniently from about 10 to about 100 ml, preferably from about 30 to about 60 ml, of organic solvent are used per 10 mmol of the phytol.

If the process is carried out in a biphasic solvent system, such as one consisting of a polar solvent, e.g., a cyclic carbonate such as ethylene or propylene carbonate, and a non-polar solvent, e.g., an aliphatic hydrocarbon such as heptane, then the volume ratio of the non-polar solvent to the polar solvent is conveniently in the range from about 0.3:1 to about 5:1, preferably from about 1:1 to about 3:2.

Moreover, the process is conveniently carried out under an inert gas atmosphere, preferably gaseous nitrogen or argon.

The actual reaction generally lasts for about 0.2 to about 20 hours, preferably about 0.5 to about 1 hour.

The process in accordance with the invention can be carried out batchwise or continuously, preferably continuously, and in general operationally in a very simple manner, for example by adding isophytol or phytol, as such or in solution, portionwise to a suspension or solution of the trimethylhydroquinone and the catalyst. The rate at which the isophytol or phytol is added is not critical. Conveniently, isophytol/phytol is added continuously over a period of about 0.2 to about 5 hours. After completion of the isophytol/phytol addition and an appropriate subsequent reaction period the working-up is effected by procedures conventionally used in organic chemistry.

If desired, the obtained (all-rac)-α-tocopherol can be converted into its acetate, succinate, poly(oxyethylene) succinate, nicotinate, and further known application forms by standard procedures.

The process in accordance with the invention enables the catalyst used to be separated readily and to be reused several times.

Advantages in the use of the catalyst in the process in accordance with the invention are, in addition to high yields of (all-rac)-α-tocopherol, the avoidance of corrosion, the avoidance of waste water contamination with heavy metal ions, the high selectivity as well as the enabled ready isolation of the produced (all-rac)-α-tocopherol from the mixture after reaction. Furthermore, the amount of dehydration products, so-called phytadienes, which tend to result from the action of acids on tertiary allylic alcohols such as isophytol and phytol, is kept to an acceptable minimum in the process of the present invention, as is the amount of furane derivatives which tend to be produced as by-products in d,1-α-tocopherol manufacture (see, for example, Bull. Chem. Soc. Japan 68, 3569–3571 (1995)).

The following examples are provided to further illustrate the method of the present invention. These examples are illustrative only and are not intended to limit the scope of the invention in any way.

EXAMPLES

Example 1

7.69 g (50 mmol) of trimethylhydroquinone were suspended or dissolved in 50 ml of toluene or diethyl ketone or in 40 ml of γ-butyrolactone or ethylene carbonate or propylene carbonate and 50 ml of heptane, whereafter 0.1 mole % (based on the amount of isophytol to be used) of the catalyst of formula I was added. Then the mixture was heated to a temperature in the range 50–150° C. and 10 g (11.9 ml; 33 mmol) of isophytol were added portionwise to the mixture over a period of about 20 minutes, all under argon. Subsequently, the reaction mixture was stirred under argon for a further 30 minutes at reflux temperature and monitored by thin layer chromatography to follow the progress of the reaction. After the establishment of completed conversion to (all-rac)-α-tocopherol this product was recovered from the reaction mixture by cooling it to about 60–80° C., separating the phases (if appropriate) and distilling off the solvent under reduced pressure.

Unambiguous identification of the product was effected by comparison of gas chromatographic retention times with those of a known sample of (all-rac)-α-tocopherol.

The results are presented in the following Table 1.

TABLE 1

Results of the use of the catalyst $(R^1SO_2)_2$ NH in the manufacture of (all-rac)-α-tocopherol using various solvents

| Catalyst | | | |
|---|---|---|---|
| $R^1$ | $R^1$ | Solvent (Amount in ml) | Yield |
| $C_2F_5$ | $C_2F_5$ | Toluene (50) | 89.6% |
| $C_2F_5$ | $C_4F_9$ | " | 90.2% |
| $CF_3$ | $C_6F_5$ | Diethyl ketone (50) | 83.8% |
| $CF_3$ | $C_6F_5$ | γ-Butyrolactone (40)/Heptane (50) | 87.4% |
| $CF_3$ | $C_4F_9$ | Ethylene carbonate (40)/Heptane (50) | 94.0% |
| $C_2F_5$ | $C_2F_5$ | " | 93.6% |
| $C_3F_7$ | $C_2F_7$ | " | 94.5% |
| $C_4F_9$ | $C_4F_9$ | " | 87.0% |
| $C_6F_5$ | $C_6F_5$ | " | 87.2% |
| $CF_3$ | $C_8F_{17}$ | Propylene carbonate (40)/Heptane (50) | 86.4% |
| $C_4F_9$ | $C_4F_9$ | " | 94.0% |
| $C_4F_9$ | $C_8F_{17}$ | " | 91.1% |
| $C_8F_{17}$ | $C_8F_{17}$ | " | 85.6% |
| $CF_3$ | $C_6F_5$ | " | 92.6% |
| $C_4F_9$ | $C_6F_5$ | " | 93.3% |
| $C_8F_{17}$ | $C_6F_5$ | " | 68.9% |
| $C_6F_5$ | $C_6F_5$ | " | 84.9% |

Using the same procedure as above with 4,4,5,5,6,6-hexafluoro-(1,3,2)dithiazinane-1,3-dioxide (formula I, in which both symbols $R^1$ together signify tri-difluoromethylene, x signifies 1 and $R^2$ signifies a proton) as the catalyst in the biphasic solvent system ethylene carbonate (40 ml) and heptane (50 ml) resulted in a 94.5% yield of (all-rac)-α-tocopherol.

Example 2

The procedure of Example 1 was repeated with the differences that 1.0 mole % of a metal containing catalyst was used, and the solvent was in all cases the biphasic solvent system 40 ml of ethylene carbonate and 50 ml of heptane. The results are presented in the following Table 2.

TABLE 2

Results of the use of the catalyst $[(R^1SO_2)_2N]_xR^2$ in the manufacture of (all-rac)-α-tocopherol

| Catalyst | | | | |
|---|---|---|---|---|
| $R^1$ | $R^1$ | $R^2$ | x | Yield |
| $C_4F_9$ | $C_4F_9$ | Ni | 2 | 91% |
| $C_4F_9$ | $C_4F_9$ | Y | 3 | 78% |
| $CF_3$ | $C_8F_{17}$ | Ag | 1 | 86% |
| $C_4F_9$ | $C_4F_9$ | Ag | 1 | 93% |
| $C_8F_{17}$ | $C_8F_{17}$ | Ag | 1 | 89% |
| $C_8F_{17}$ | $C_6F_5$ | Ag | 1 | 89% |
| $C_4F_9$ | $C_4F_9$ | Tm | 3 | 90% |

Using the same procedure as above with the silver salt of 4,4,5,5,6,6-hexafluoro-(1,3,2)dithiazinane-1,3-dioxide (formula I, in which both symbols $R^1$ together signify tri-difluoromethylene, x signifies 1 and $R^2$ signifies the silver cation) as the catalyst resulted in a 88% yield of (all-rac)-α-tocopherol.

The invention being thus described, it will be obvious that the same may be varied in many ways. Such variations are not to be regarded as a departure from the spirit and scope of the invention and all such modifications are intended to be included within the scope of the following claims.

What is claimed is:

1. A method of making (all-rac)-α-tocopherol in a reaction mixture comprising:
    a) reacting trimethylhydroquinone and a phytol selected from the group consisting of isophytol and phytol in the presence of a bis(perfluorinated hydrocarbyl sulphonyl) imide catalyst or a metal salt thereof of formula I:

$$[(R^1SO_2)_2N]_xR^2 \qquad (I)$$

wherein
    each $R^1$, independently, signifies a perfluoroalkyl group $C_nF_{2n+1}$ or a pentafluorophenyl, or both symbols $R^1$ together signify a poly-difluoromethylene group— $(CF_2)_m$—, with the proviso that both symbols $R^1$ cannot simultaneously signify trifluoromethyl,
    $R^2$ signifies a proton or a cationic form of a metal selected from the group consisting of boron, magnesium, aluminium, silicon, scandium, titanium, vanadium, manganese, iron, cobalt, nickel, copper, zinc, yttrium, zirconium, rhodium, palladium, silver, tin, lanthanum, cerium, praseodymium, neodymium, europium, dysprosium, thulium, ytterbium, hafnium, platinum, and gold,
    m is an integer from 2 to 4,
    n is an integer from 1 to 10, and
    x is the corresponding valency of the proton (1) or the metal cation (1, 2, 3, or 4), in organic solvent; and
    b) recovering (all-rac)-α-tocopherol from the reaction mixture.

2. A method according to claim 1 wherein the organic solvent is selected from the group consisting of an aliphatic or cyclic ketone, an aliphatic or cyclic ester, and an aliphatic or aromatic hydrocarbon.

3. A method according to claim 2 wherein the solvent is selected from the group consisting of diethyl ketone, isobutyl methyl ketone, cyclopentanone, isophorone, ethyl acetate, isopropyl acetate, γ-butyrolactone, ethylene carbonate, propylene carbonate, hexane, heptane, octane, benzene, toluene, and xylene.

4. A method according to claim 1 wherein the bis (perfluorinated hydrocarbyl sulphonyl)imide or metal salt thereof of formula I is present in the reaction mixture at from about 0.01 mole % to about 4 mole % based on the amount of trimethylhydroquinone or phytol present in the reaction mixture, whichever is in the lesser molar amount.

5. A method according to claim 1 further comprising selecting a metal salt of formula I as the catalyst and adding a Bronsted acid as a co-catalyst to the reaction mixture.

6. A method according to claim 5 wherein the Bronsted acid is selected from the group consisting of sulphuric acid, phosphoric acid, and p-toluenesulphonic acid.

7. A method according to claim 5 wherein from about 0.01 mole % to about 0.5 mole % of the metal salt of formula I is added to the mixture.

8. A method according to claim 1 wherein about 10 to about 100 ml of organic solvent are added to the reaction mixture per 10 mmol of the phytol.

9. A method according to claim 8 wherein about 30 to about 60 ml of organic solvent are added to the reaction mixture per 10 mmol of the phytol.

10. A method according to claim 1 further comprising carrying out the reaction at from about 50° C. to about 150° C.

11. A method according to claim 10 wherein the reaction is carried out at from about 90° C. to about 125° C.

12. A method according to claim 11 wherein the reaction carried out at from about 105° C. to about 120° C.

13. A method according to claim 1 wherein the molar ratio of trimethylhydroquinone to phytol present in the reaction mixture is from about 1.3:1 to about 2.5:1.

14. A method according to claim 13 wherein the molar ratio is from about from about 1.5:1 to about 2.2:1.

15. A method according to claim 14 wherein the molar ratio is about 2:1.

16. A method according to claim 1 wherein the phytol is added portionwise to a suspension or solution of the trimethylhydroquinone and the catalyst.

17. A method according to claim 1 wherein the organic solvent is a biphasic solvent system comprising a non-polar and a polar solvent.

18. A method according to claim 17 wherein the volume ratio of non-polar solvent to polar solvent is from about 0.3:1 to about 5:1.

19. A method according to claim 17 wherein the volume ratio of non-polar solvent to polar solvent is from about 1:1 to about 3:2.

20. A method according to claim 1 further comprising converting the (all-rac)-α-tocopherol into a salt selected from the group consisting of acetate, succinate, poly(oxyethylene)succinate, and nicotinate.

* * * * *